United States Patent [19]
von Roos

[11] Patent Number: 4,661,770
[45] Date of Patent: Apr. 28, 1987

[54] METHOD AND APPARATUS FOR MEASURING MINORITY CARRIER LIFETIME IN A DIRECT BAND-GAP SEMICONDUCTOR

[75] Inventor: Oldwig von Roos, So. Pasadena, Calif.

[73] Assignee: The United States of America as represented by the Administrator of the National Aeronautics and Space Administration, Washington, D.C.

[21] Appl. No.: 683,111

[22] Filed: Dec. 18, 1984

[51] Int. Cl.$^4$ .......................................... G01R 31/26
[52] U.S. Cl. ........................... 324/158 D; 324/158 R
[58] Field of Search ............... 324/77 H, 77 K, 79 R, 324/79 D, 96, 158 D, 158 R, 158 T; 250/461.1

[56] References Cited

U.S. PATENT DOCUMENTS

| | | | |
|---|---|---|---|
| 3,886,370 | 5/1975 | Schubert et al. | 324/158 D |
| 3,919,639 | 11/1975 | Graff et al. | 324/158 R |
| 3,982,184 | 9/1976 | Sanderson | 324/79 D |
| 4,122,383 | 10/1978 | von Roos | 324/20 R |
| 4,286,215 | 8/1981 | Miller | 324/158 R |
| 4,374,328 | 2/1983 | Tekippe et al. | 250/461.1 |
| 4,551,674 | 11/1985 | Miller | 324/158 R |

FOREIGN PATENT DOCUMENTS 1894452  1/1976  U.S.S.R. .......................... 324/79 R

OTHER PUBLICATIONS

"Two-Chopper Technique for Measuring Fluorescence Lifetimes", by Ingersoll, 1/76, Applied Optics, vol. 15, #1, pp. 61–63.
O. von Roos, J. Appl. Phys. 50, 3738 (1979).
Weiner et al., J. Appl. Phys. 55, 3889 (1984).
O. von Roos, J. Appl. Phys. 54, 1389, 2495 (1983).

Primary Examiner—Reinhard J. Eisenzopf
Assistant Examiner—W. Burns
Attorney, Agent, or Firm—Paul F. McCaul; John R. Manning; Thomas H. Jones

[57] ABSTRACT

A direct band-gap semiconductor (54) is exposed to intensity-modulated photon radiation (56) having a characteristic energy at least as great as the energy gap of the semiconductor. This produces a time-dependent concentration of excess charge carriers through the material, producing a luminescence signal (58) modulated at the same frequency as the incident radiation but shifted in phase by an amount related to the lifetime of minority carriers. In a preferred embodiment, the phase shift of the luminescence signal is determined by transforming it to a modulated electrical signal and mixing the electrical signal with a reference signal modulated at the same frequency and having a phase which is known relative to the incident radiation. Minority carrier lifetime is calculated by integrating a direct current component of the mixed signal ($F_{dc}$) over a $2\pi$ range in phase of the reference signal.

14 Claims, 3 Drawing Figures

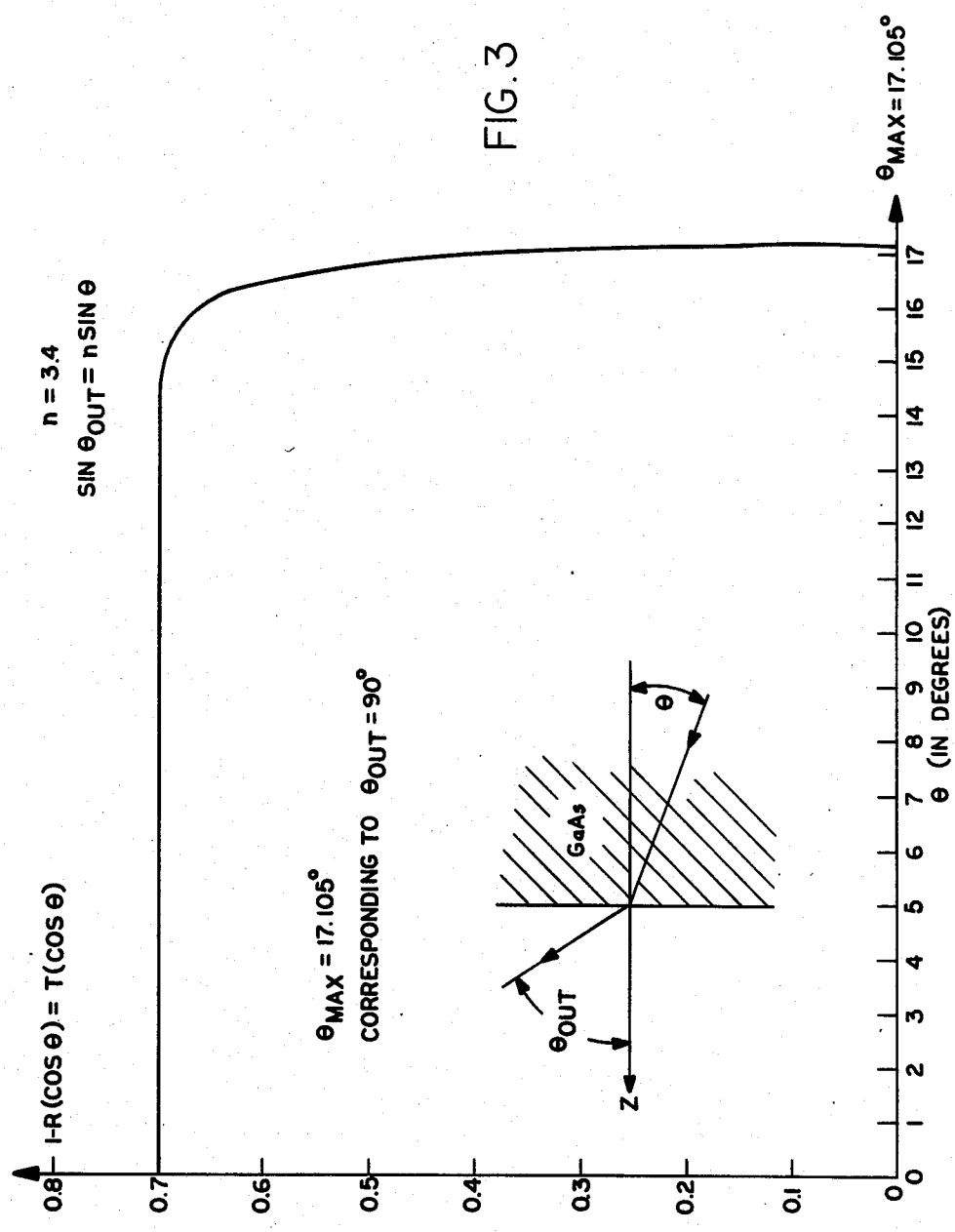

METHOD AND APPARATUS FOR MEASURING MINORITY CARRIER LIFETIME IN A DIRECT BAND-GAP SEMICONDUCTOR

ORIGIN OF THE INVENTION

The invention described herein was made in the performance of work under a NASA contract and is subject to the provisions of PL 96-517 (35 USC Section 202) with the Contractor not electing to retain title.

TECHNICAL FIELD

The present invention relates to the field of solid state electronics and, more particularly, to the nondestructive measurement of minority carrier lifetimes in direct band-gap semiconductors.

BACKGROUND OF THE INVENTION

Direct band-gap semiconductors, such as gallium aresenide (GaAs), are useful, in a variety of devices. Two such devices, solar cells and fast computer switches, call for material of vastly different electrical properties, including the Shockley-Read-Hall lifetime ($\tau_{SRH}$) of minority carriers. In solar cells, series resistance must be minimized to maximize output current. A longer lifetime permits charge carriers to move greater distances before recombination, reducing series resistance. However, rapid current decay is important in high speed switching, and short carrier lifetimes enhance current decay.

Prior attempts to measure minority carrier lifetimes in semiconductors are described in: O. von Roos, J. Appl. Phys. 50, 3738 (1979); U.S. Pat. No. 4,122,383, O. von Roos; and Weiner, et al., J. Appl. Phys. 55, 3889 (1984).

In the methods of the von Roos publications, devices containing p-n junctions are irradiated by electron beams or monochromatic light to measure minority carrier lifetime. These methods are "destructive" of the sample in the sense that a p-n junction must be formed and ohmic contacts must be applied to measure an electrical signal. In the Weiner, et al. article, a short pulse of incoming laser light is applied to GaAs to trigger a luminescence pulse which decays in a characteristic time. Carrier lifetime is calculated from the decay time. The Weiner et al. method is nondestructive of the material, but is aperiodic and does not provide the accuracy desired in carrier lifetime measurements.

The impact of radiative recombination and the reabsorption of recombination radiation on minority-carrier transport in direct band-gap semiconductors has been explored in the following publications: O. von Roos, J. Appl. Phys. 54, 1390 (1983); and O. von Roos, J. Appl. Phys. 54, 2495 (1983). However, they do not treat the time dependent case and do not propose a means for measuring lifetime.

Therefore, it is desirable to provide a method for accurately measuring minority carrier lifetime in a homogeneous sample of a direct band-gap semiconductor, without altering the sample material by introducing a p-n junction or applying ohmic contacts to it.

STATEMENT OF THE INVENTION

The present invention provides a method and apparatus for measuring minority carrier lifetime in a direct band-gap semiconductor having a preselected energy gap. The method comprises: producing luminescence radiation within a sample of the semiconductor by irradiating the sample with incident photon radiation having a characteristic energy at least as great as the energy gap; modulating the intensity of the incident radiation to induce modulation of the luminescence radiation at a phase shifted from the incident radiation; detecting the luminescence radiation; and isolating information as to the amount by which the phase of the luminescence radiation is shifted, as a measure of minority carrier lifetime.

In a preferred embodiment, the phase shift of the luminescence radiation is measured relative to a reference signal modulated at the same frequency as the incident radiation but different in phase therefrom. More specifically, an electrical signal derived from luminescence is mixed with a modulated reference signal having a phase which is known relative to the phase of the incident radiation.

In another preferred embodiment, the direct band-gap semiconductor is chosen from the group consisting of GaAs, $Al_xGa_{(1-x)}As$ ($x<0.44$), InP, GaSb, and InAs, and is preferably GaAs.

The invention makes use of the fact that, although radiative recombination of electron-hole pairs is fast in direct band-gap semiconductors, its influence on bulk carrier transport is small. Such recombination expresses itself as a renormalization of the diffusion constant which is noticable only at high doping levels ($N_A > 10^{18}$ cm$^{-3}$ for n-type GaAs). In addition, the luminescence radiation contemplated herein is strictly that due to band-band transition at room temperature. All other radiative processes, such as band-donor, band-acceptor, donor-acceptor and other transitions, can be ignored since they occur predominantly at low temperatures. In any case, band-band transitions constitute the vast majority of all photon processes in nonequilibrium direct band-gap semiconductors.

In the method of the present invention, incident radiation having a photon energy well above the band-gap energy of the semiconductor is modulated in intensity at a preselected frequency. Photoluminescence radiation induced in the sample is modulated at the same frequency, but is shifted in phase relative to the incident radiation.

The luminescence signal is transformed to an electrical signal and mixed with a modulated reference signal, which may be derived from the power supply used to generate the incident radiation. The reference signal is modulated at the same frequency as the incident radiation, and the phase of the reference signal is variable. Because the two signals are of the same frequency, mixing produces an output having a dc component which contains information as to the difference in phase. After the dc component is isolated and integrated over a $2\pi$ range in phase of the reference signal, a simple calculation yields the minority carrier lifetime to a high degree of accuracy.

The method of the present invention is highly accurate, but is not destructive of the sample. It can be performed on any exposed surface of a direct band-gap semiconductor, and can be used either for quality control in the manufacture of semiconductive material or to characterize existing material and devices.

BRIEF DESCRIPTION OF THE DRAWINGS

The above and other features of the present invention may be more fully understood from the following detailed description, together with the accompanying drawings, wherein similar reference characters refer to similar elements throughout and in which:

FIG. 3 is a graphical representation of the transmissivity of a sample of GaAs to luminescence radiation in the outgoing direction, as a function of angle.

DETAILED DESCRIPTION OF THE INVENTION

Figure 1:
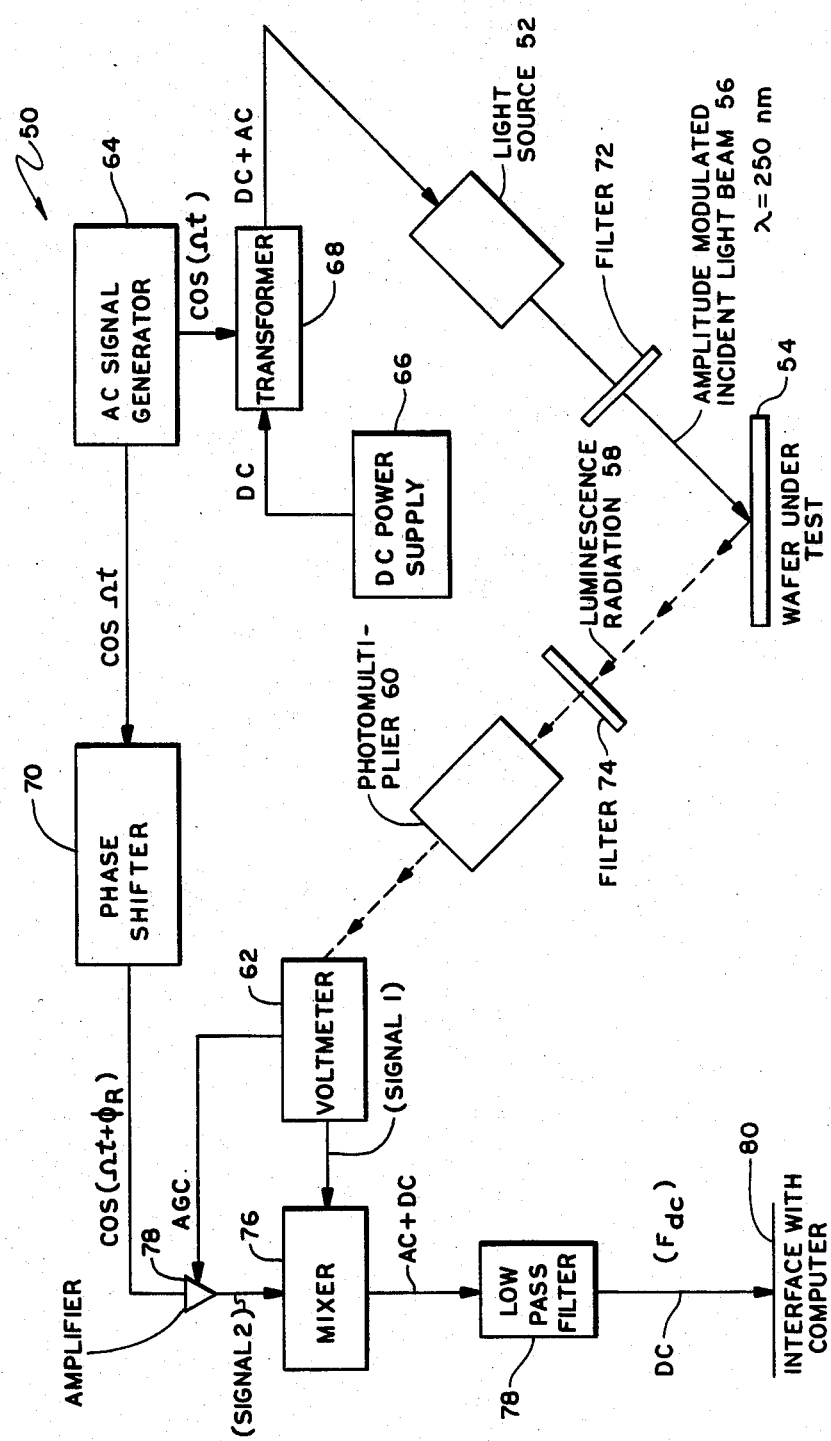
FIG. 1 is a schematic representation of an apparatus useful in performing minority carrier lifetime determinations according to a preferred form of the present invention.

Referring now to the drawings, specifically FIG. 1, one form of measurement apparatus 50 constructed according to the present invention comprises a light source 52 irradiating a sample wafer 54 with an amplitude modulated incident light beam 56, such that photoluminescence radiation 58 is emitted at the same modulation frequency as the incident beam but at a phase shifted therefrom. The luminescence radiation 58 is transformed to a suitable electrical signal by a photomultiplier 60 and a volt meter 62, and is mixed with a reference electrical signal which is modulated at the same frequency as the incident light beam and has a known phase relationship to the incident beam. Because the two mixed signals are modulated at the same frequency, the output has a dc component representative of the phase shift between them. The dc component is isolated, summed over an angle of $2\pi$ radians in the phase of the reference signal, and used to calculate minority carrier lifetime.

Referring to the system of FIG. 1 in greater detail, the light source 52 is driven by an ac generator 64 and a dc power supply 66, both acting through a transformer 68 to apply a combined signal of the general form: $V = V_0 + V_1 \cos \Omega t$. The generator 64 provides a second (reference) ac signal to a phase shifter 70. The element 70 shifts the phase of the reference signal by a variable angle ($\phi_R$) producing an output having an amplitude modulated as $\cos (\Omega t + \phi_R)$.

When the material being measured is GaAs, the light source 52 may be a mercury discharge lamp having a characteristic wavelength of 250 nanometers (approximately 5 electron volts) and arranged to illuminate a spot approximately 1 square centimeter in area. The dc component ($V_0$) of the applied voltage keeps the source 52 within its operating range, while the ac component ($V_1 \cos \Omega t$) modulates the intensity of the light produced. The light beam 56 from the source 52 takes the form $I_0 + I_1 \cos \Omega t$, with $I_0$ representing the average intensity and $I_1$ the amplitude of modulation. Typically, the beam is passed through one or more filters 72 before it reaches the sample.

Alternatively, the light source 52 can be a laser or other light source which is suitably coherent and monochromatic, as long as the light produced by the source has a photon energy above the band-gap of the semiconductor material to be measured. For GaAs, the energy must be greater than 1.43 electron volts.

When the intensity modulated light beam 56 impinges on the sample, a portion is absorbed by the sample and generates free charge carriers therein. The carriers diffuse throughout the sample, their densities being modulated by the frequency ($\Omega$) at which the intensity of the light beam is modulated. As the carriers diffuse, the emit characteristic luminescence radiation which is similarly modulated. Owing to a time lag between diffusion and the filling and the emptying of recombination centers, the diffusion current and the luminescence radiation exhibit a characteristic phase shift $\phi$ with respect to the externally applied radiation. The phase shift depends on the Shockley-Read-Hall lifetime ($\tau_{SRH}$) of minority carriers and other important parameters of the material, including surface recombination velocity (s) and absorption coefficient ($\alpha$). The surface recombination velocity affects the phase shift of the luminescence radiation only slightly when the surface recombination velocity is very large.

In the present method, some of the luminescence radiation escapes outwardly through the surface of the sample, where it can be measured. The range of angles over which radiation escapes is illustrated in FIG. 3, which depicts transmittance as a function of the angle made by outgoing radiation with the normal to the sample surface. Ultimately, the range depends upon the index of refraction of the sample for the frequency of luminescence radiation. In the case of GaAs, radiation escapes only if the angle with the normal direction is between 0 and 17.105 degrees.

The intensity of the luminescence radiation is modulated at the same frequency ($\Omega$) as the incident light beam. Only the phase of the modulation and the photon energy are different.

The luminescence radiation 58 is passed through a filter 74 to the photomultiplier 60, where it is transformed to an electrical current modulated with the same frequency and having the same phase as the luminescence signal. The filter 74 blocks out noise and reflected light by passing only luminescence radiation of approximately 1.45 electron volts.

The signal from the photomultiplier 60 is applied to the volt meter 62, which generates a primary voltage signal (signal 1) applied to a mixer 76 and an AGC (automatic gain control) signal applied to an amplifier 78. The amplifier 78 amplifies the reference signal ($\cos (\Omega t + \phi_R)$) according to the magnitude of the AGC signal, and the output (signal 2) is applied to a second input of the mixer 76. The AGC signal, in combination with the amplifier 78, causes signal 2 to be equal in peak amplitude to signal 1.

Signals 1 and 2 are modulated at the same frequency as the intensity of the incident light, but are each shifted in phase from it. Signal 1 is shifted in phase by an amount determined by the minority carrier lifetime of the sample material, and signal 2 is shifted by the angle $\phi_R$.

The mixer 76 may be a heterodyne circuit of the type found in television and radio sets, effectively "multiplying" the two periodic input signals. Thus, the output or "mixed" signal has components representing the sum and difference, respectively, of the frequencies at which the input signals are modulated. Because the frequencies of the input signals are the same, the output has an ac component of twice the original frequency and a dc component representing the difference in phase between the signals. The mixing operation can be understood in terms of the following product of two sinusoidal signals which differ only in phase:

$$\cos(\Omega t + \phi_1) \cdot \cos(\Omega t + \phi_2) = \tfrac{1}{2}[\cos(2\Omega t + \phi_1 + \phi_2) + \cos(\phi_1 - \phi_2)]$$

The first term of the product represents the ac component of the "mixed" signal, while the time-independent second term represents the dc component ($F_{dc}$). The dc component is isolated by a conventional low pass filter 78. The signal is then converted to digital form and interfaced with a computer, as indicated at 80 of FIG. 1, for calculation of minority carrier lifetime.

Minority carrier lifetime is calculated by performing the following integrations:

$$\frac{1}{\pi} \int_{\alpha}^{2\pi + \alpha} \cos\phi \, F_{dc} \, d\phi = F_1(\Omega), \quad (I)$$

(equation 29a, below)

$$\frac{1}{\pi} \int_{\alpha}^{\alpha + 2\pi} \sin\phi \, F_{dc} \, d\phi = F_2(\Omega). \quad (II)$$

(equation 29b, below)

The integrations are performed by measuring $F_{dc}$ at different angles in the phase of the reference signal, and numerically integrating over a $2\pi$ range. The resultant quantities, $F_1(\omega)$ and $F_2(\omega)$, are then substituted into the equation $$\Omega \tau_p = \frac{2}{\eta} F_2 F_1^{-2} \quad (III)$$

(equation 31, below)

for determination of $\Omega \tau_p$, where $\tau_p$ is defined as $\tau_{SRH}$ for holes in an n-type sample. In a p-type sample, the relevant quantity would be $\tau_n$, but the expressions (I), (II), and (III) would be similar. In either case, division of $\Omega \tau$ by the frequency yields the desired quantity, $\tau$.

Equation (III) is based on the assumption that $\Omega \tau$ is small. If the quantity $\Omega \tau$ turns out to be too large to support the approximation, the procedure can be repeated at a different (lower) modulation frequency.

Once the sample is positioned relative to the apparatus 50, the signal generator 64, power supply 66 and transformer 68 are activated to illuminate a portion of the sample with intensity modulated light of desired photon energy, intensity and modulation frequency. The luminescence radiation produced in the sample is detected by the photomultiplier and transformed to an electrical signal of similar modulation frequency and phase. The electrical signal is "mixed" by the element 76 with a sinusoidal reference signal of the same frequency, producing a mixed signal having a dc component ($F_{dc}$) which contains phase information. The quantities $F_1$ and $F_2$ are obtained by integrating $F_{dc}$ over a $2\pi$ range in the phase of the reference signal. The phase shifter 70 may be controlled by the computer (interfaced at 80 in FIG. 1) to perform the required numerical integration, after which the computer uses the quantities $F_1$ and $F_2$ to solve the equation (III) for $\tau_p$.

The mathematical expressions (I), (II) and (III) are derived by assuming a homogeneously doped n-type sample of GaAs having dimensions which are large compared to the diffusion length of minority carriers. Since diffusion lengths in n-type GaAs are generally less than 5 microns, an epitaxially grown layer of extrinsic GaAs having a thickness of 50 microns may be considered an "infinite" sample as far as diffusion of carriers is concerned. A similar approximation holds true for the absorption coefficient ($\alpha$) when doping is not too high. For $N_D < 5 \times 10^{18}$ cm$^{-3}$, $\alpha$ drops from a high value of $10^4$ cm$^{-1}$ to 10 cm$^{-1}$ over a comparatively small range of energies, so that the approximations used in O. von Roos, J. Appl. Phys. 54, 1390 (1983), are also applicable. Those approximations include: (a) treatment of the sample as an infinitely extended body; and (b) representation of the absorption coefficient as a step function over the angular frequency, as far as hole transport is concerned.

A 50 micron thick layer of extrinsic GaAs can be treated as an infinitely extended sample for purposes of photon transport by radiative transfer, even for photons possessing an absorption coefficient ($\alpha$) of approximately 100 cm$^{-1}$, because the extrinsic layer is grown epitaxially on a substrate of intrinsic or compensated GaAs many mils thick and the refractive indices of extrinsic and intrinsic GaAs differ very little. Consequently, there is negligible reflection at the extrinsic-intrinsic interface and all photons passing to the substrate will be absorbed there.

A simple analysis shows that equations (33) of O. von Roos, J. Appl. Phys. 54, 1390 (1983) for the photon distribution function (f$_-$) may be used, provided that the limit (infinity) on all integrals is replaced by W, the thickness of the extrinsic layer. The result for the component of the radiation field which travels toward the surface is $$f_-(z, \eta, \omega) = \eta^{-1} \alpha(\omega) P_0 \, {}^1 e^{-\hbar\omega/kT} \cdot \mu^{-2} e^{-\alpha(z-z')/\eta} p(z') dz' \quad (1)$$

This expression is valid for $\eta = \cos\theta < 0$. The notation is the same as in O. von Roos, J. Appl. Phys. 54, 1390 (1983), and is depicted generally in FIG. 1. The function $p(z')$ is the excess hole concentration, which is time independent, and $P_0$ is the equilibrium value of the hole concentration. We also assume that the exciting light possesses an angular frequency ($\omega_1$) which is such that the quantity $\alpha(\omega_1)$ is greater than $10^4$ cm$^{-1}$. By equation 56 of O. von Roos, id., we know that $p(z)$ behaves as $a_1 e^{-\alpha(\omega_1)z/\eta_1} + a_2 e^{-z/L}$. Therefore, replacing the integration limit W with infinity constitutes a negligible error, proving the validity of the assumption of an infinitely extended sample.

In order to fully utilize the theory of O. von Roos, id., one more condition must be met. The beam of monochromatic light at the frequency $\omega_1$ must illuminate uniformly a surface area which is large compared to the diffusion length L of the carriers. In that case, edge effects at the boundary between illuminated and dark semiconductor material may be neglected and a one-dimensional analysis may be applied, provided that the emerging luminescence radiation is sampled from the vicinity of the center of the light spot.

The following discussion implements the theory developed in O. von Roos, id., suitably modified for the time-dependent case, in accordance with the assumptions set forth above. An incident photon flux impinging on the semiconductor surface, as indicated in FIG. 1, is given by the real part of $$N_{80} = N_\lambda^{(0)} + N_\lambda^{(1)} e^{-i\Omega t} \quad (2)$$

The photon flux $N_\lambda$, in units of cm$^{-2}$ sec$^{-1}$, is modulated with angular frequency $\Omega$ and makes the angle $\theta_0$ with the normal to the surface. The angle $\theta_1$ between the direction of the flux inside the sample and the normal to the sample surface is given by the approximate relationship $$\sin \theta_1 = n_1^{-1} \sin \theta_0 \tag{3}$$

where $n_1$ is the refractive index at the light frequency $\omega_1$. Equation (3) is only approximate since the extinction coefficient $\kappa$ is non-zero, particularly for large frequencies. For a photon energy of 5 eV ($\omega_1 = 7.583 \times 10^{15}$ sec$^{-1}$) and a sample of GaAs, we have $n_1 = 2.273$ and $\kappa_1 = 4.084$. The exact connection between $\theta_0$ and $\theta_1$ in such a case is given by Born and Wolf, Principles of Optics, 5th Ed. Pergamon Press, Oxford p. 616 (1975). However, calculations show for the above-quoted values of $n_1$ and $\kappa_1$ that the difference between the correct angle $\theta_1$, and the angle $\theta_1$ obtained from equation (3) is only 0.5 degrees for $\theta_0 = 40$ degrees, and 2 degrees for $\theta_0 = 80$ degrees.

Keeping in mind the derivation of the diffusion equation for holes given in O. von Roos, J. Appl. Phys. 54, 1390 (1983), and the assumptions discussed above, the excess hole concentratin p can be determined from the relation $$(D_p + D_R)\frac{\partial^2 p}{\partial z^2} - \frac{p}{\tau_p} = \tag{4}$$

$$\frac{\partial p}{\partial t} - [1 - R(|\eta_1|)]\alpha_1 e^{-\alpha_1 z/\eta_1}(N_\lambda^{(0)} + N_\lambda^{(1)} e^{-i\Omega t}).$$

$D_R$ is the radiative diffusion constant (equation (43a) of O. von Roos, id.) and $\tau_p$ is the Shockley-Read-Hall lifetime.

The question of whether $\tau_p$ of equation (4) for time-dependent cases is the same as the usual expression for the Shockley-Read-Hall lifetime for the steady state case has been analyzed for low level injection conditions in O. von Roos, J. Appl. Phys. 51, 4523 (1980). Although the referenced work concerned itself mainly with silicon, the analysis holds fo GaAs, as well. That is, $\tau_p$ of the time-dependent equation (4) signifies the steady state lifetime, provided that the density of recombination centers ($N_t$) is small compared to the equilibrium electron density ($N_0$) and that the energy levels of the recombination centers lie near mid-gap. Since the density of donors in n-type GaAs is greater than or equal to $10^{17}$ cm$^{-3}$, the first condition is usually satisfied. We assume the second condition also to be satisfied, as it is with Fe, Cr or O in GaAs.

Turning to equation (4), we substitute $$p = p_0(z) + p_1(z) e^{-i\Omega t} \tag{5}$$

and obtain for the ac component ($p_1$) the following equation $$\frac{d^2 p_1}{dz^2} + \frac{p_1}{L'^2} = -D^{-1} \alpha_1 N_\lambda^{(1)} (1 - R(|\eta_1|)) e^{-\alpha_1 z/\eta_1}. \tag{6}$$

Here we have defined $$D = D_p + D_R;$$

$$L' = [(D_p + D_R)\tau_p(1 - i\Omega\tau_p)^{-1}]^{\frac{1}{2}} = L(1 - i\Omega\tau_p)^{-\frac{1}{2}} \tag{7}$$

As the boundray condition at the surface $z = 0$ (see FIG. 1), we take $$D_p \frac{dp_1}{dz} = sp_1 \text{ at } z = 0 \tag{7'}$$

The surface recombination velocity (s) is rather large for GaAs (s > $10^6$ cm/sec) and overwhelms all effects of the recombination radiation at the surface, as shown in O. von Roos, J. Appl. Phys., 54, 1390 (1983). The solution of equations (6) and (7) is then given by:

$$p_1 = (1 - R(\eta_1)) \alpha_1 L'^2 N_\lambda^{(1)} D^{-1} \times \tag{8}$$

$$[1 - (\alpha_1 L'/\eta_1)^2]^{-1} \left( e^{-\alpha_1 z/\eta_1} - \frac{\alpha_1 L' + \xi}{1 + \xi} e^{-z/L'} \right).$$

where $\xi = L's/D_p$ \hfill (9)

The actual excess hole number density is given by the real part of $p_1 \cdot e^{-i\Omega t}$.

The modulated luminescence signal emerging from the sample is then determined as follows, starting with the radiative transfer expression given as equation (25) of O. von Roos, id.:

$$\left( c_g^{-1} \frac{\partial}{\partial t} + \eta \frac{\partial}{\partial z} \right) f = \alpha(\omega) (e^{-\hbar\omega/kT} p/P_0 - f). \tag{10}$$

Substituting
$$f = f_1 e^{-i\Omega t} \text{ and } p = p_1 e^{-i\Omega t}. \tag{11}$$

yields:

$$\eta \frac{df_1}{dz} = \alpha e^{-\hbar\omega/kT} p_1/P_0 - (\alpha - i\Omega/c_g) f_1. \tag{12}$$

But $c_g = c/n$, where n is the refractive index at the frequency $\Omega$, and $$\alpha >> n\Omega/c \tag{13}$$

because $\alpha$ above the band gap is much larger than 100 cm$^{-1}$ for the frequencies of interest and $n\Omega/c < 0.1$ cm$^{-1}$ (using n = 3, $\Omega < 1$ GHz and $c = 3 \times 10^{10}$ cm/sec). The flux of radiation just inside the sample at the surface $z = 0$, going in the direction $\theta > 90$ degrees (toward the outside) and crossing the surface, is given as $$|\eta| F(\omega, \eta, t) d\omega d\Omega = \frac{n^2 \omega^2}{4\pi^3 c^2} f_-(0, \eta, \omega, t) d\omega |\eta| d\Omega \tag{14}$$

where $$f_-(0, \eta, \omega, t) = \tag{15}$$

$$-\eta^{-1} P_0^{-1} e^{-\hbar\omega/kT} \alpha \int_0^\infty e^{\alpha z/\eta} Re\{p_1(z) e^{-i\Omega t}\} dz$$

for $\eta < 0$. In equation (15), the integral extends to infinity, for the reasons discussed above. The term $d\Omega$ signifies a solid angle element $\sin \theta \, d\theta \, d\phi$ inside the semiconductor.

According to Snell's law,
$$n\sqrt{1-\eta^2} = n \sin \theta = \sin \theta_{out}. \tag{16}$$

With $\theta_{out}$ representing the angle between the direction of luminescence radiation and the outward normal to the surface of the semiconductor, we obtain $$|\eta| d\Omega = n^{-2} \cos \theta_{out} d\Omega_{out}. \quad (17)$$

Therefore, the flux of radiation in the direction $(\theta_{out}, \phi)$ outside the semiconductor is given by $$\cos \theta_{out} F_{out}(\omega, \theta_{out}, t) d\omega d\Omega_{out} = n^{-2}[1 - R(|\eta|)]F(\omega, \eta, t)d\omega \cos \theta_{out} d\Omega_{out}. \quad (18)$$

Figure 2:
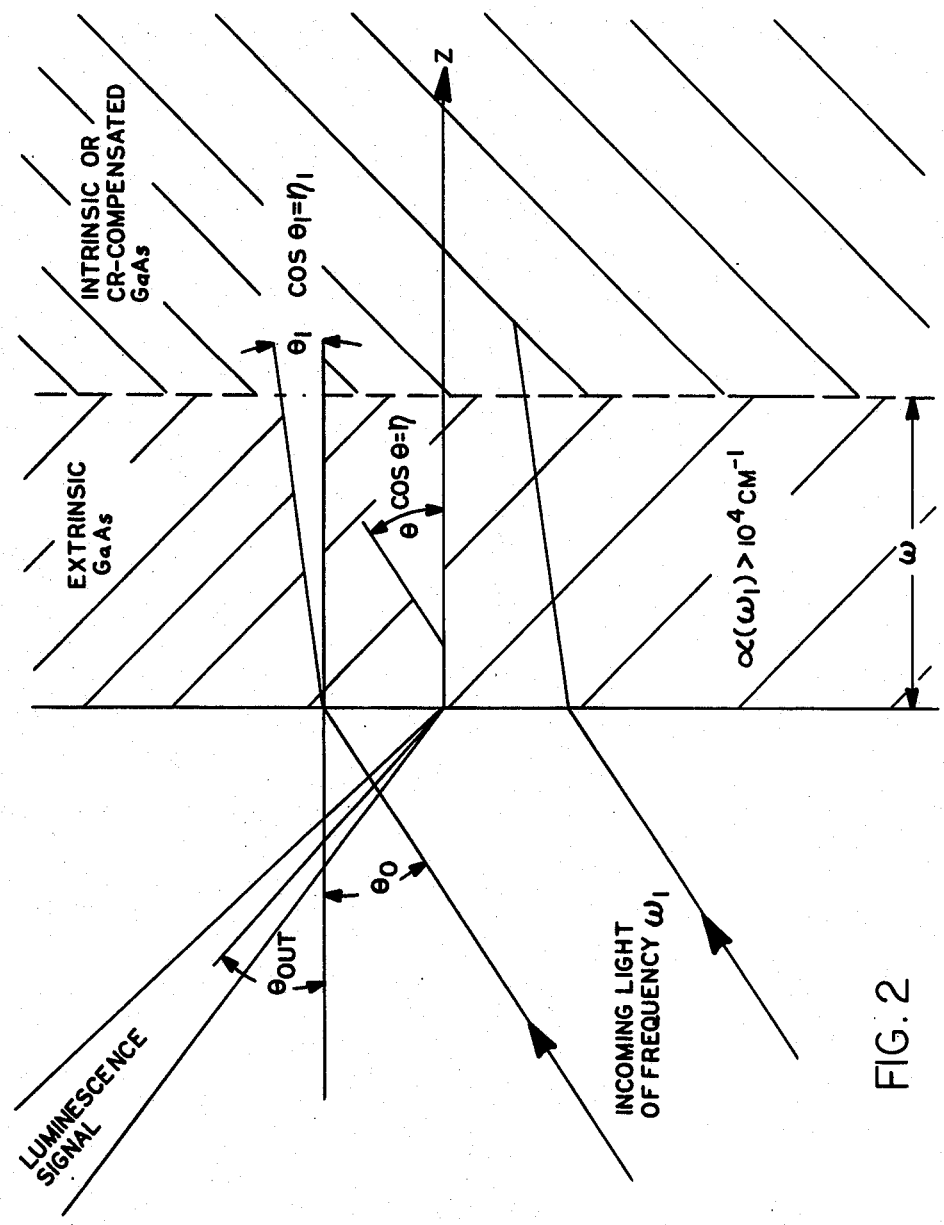
FIG. 2 is a diagrammatic cross-sectional view of a sample of a direct band-gap semiconductor undergoing a minority carrier lifetime determination according to the method of the present invention.

For $\kappa \cong 0$ and unpolarized light, it can be shown that $$1 - R(|\eta|) = \frac{4n}{(n+1)^2} \quad (19)$$

independent of angle. This is shown in FIG. 2 for n=3.4. A rapid drop of the transmissivity, 1−R, can be seen to occur between $\theta=16$ degrees and $\theta=17.1$ degrees, corresponding to $\theta_{out}=70$ degrees and $\theta_{out}=90$ degrees, respectively. The results (18) and (19) presented here are in agreement with work described at J. Vilms, et al., J. Appl. Phys., 36, 2815 (1965), with $n^{-2}(1-R(|\eta|)) \cos \theta_{out} d\Omega_{out}$ being essentially the factor $f_c$ of that reference.

Redefining the angle $\theta$ according to the inset of FIG. 2, we have $-\eta = \cos \theta > 0$, since now the z-axis points in the direction of the outward normal. Substituting equation (8) into equation (15), performing the integration and collecting all terms, we obtain the final result for the flux of luminescence radiation per frequency $d\omega$ and per solid angle outside the semi-conductor:

$$\frac{dF_1}{d\omega \, d\Omega_{out}} = \quad (20)$$

$$[1 - R(\eta_1)][1 - R(\eta)] \frac{\omega^2 \alpha_1 \alpha}{4\pi^3 c^2 D P_0} \cos(\theta_{out}) e^{-\hbar\omega/kT} \times$$

$$N^{(1)} Re \left\{ \frac{L'^2}{1 - (\alpha_1 L'/\eta_1)^2} \left[ \left( \frac{\alpha_1}{\eta_1} + \frac{\alpha}{\eta} \right)^{-1} - \frac{\alpha_1 L' + \xi}{1 + \xi} \left( \frac{\alpha}{\eta} + \frac{1}{L'} \right)^{-1} \right] e^{-i\Omega t} \right\}$$

This is the number of photons emerging from the sample per frequency and solid angle, moving in the direction $\theta_{out}$ and $\phi$.

The connection between $\eta = \cos \theta$ and $\theta_{out}$ is given by equation (16). $L'$ is defined by equation (7) and $\xi$ is defined by equation (9). Since the surface recombination velocity (s) is usually quite large, the absolute value of $\xi$ is also large compared to unity (for L=2 microns, $s=10^6$ cm/sec and D=5 cm$^2$/sec, Ls/D$_p$=40, for instance). In this case, $$\frac{\alpha_1 L' + \xi}{1 + \xi} = 1 + \frac{\alpha_1 D_p}{s} \quad (21)$$

At a photon energy of 5 eV (0.25 micron wavelength), the absorption coefficient, ($\alpha_1$) has a maximum value for GaAs of $\alpha_1 = 2 \times 10^6$ cm$^{-1}$. The expression (20) then can be simplified considerably, yielding for the term in braces of equation (20)

$$Re\{\} = \frac{\eta_1^2 \eta}{\alpha_1^2}\left(1 + \frac{\alpha_1 D_p}{s}\right) Re\left\{\frac{L'}{1 + \alpha L'} e^{-i\Omega t}\right\}. \quad (22)$$

Using equations (7), (19) and (20), we obtain the following result for the case of large s and $\alpha_1$:

$$\frac{dF_1}{d\omega \, d\Omega_{out}} = (1 - R(\eta_1)) \frac{n \omega^2 \alpha L \, \eta \, \eta_1^2}{\pi^3 c^2 D P_0 \alpha_1 (n+1)^2} \times \quad (23)$$

$$\left(1 + \frac{\alpha_1 D_p}{s}\right) N_\lambda^{(1)} e^{-\hbar\omega/kT} \cos(\theta_{out}) \times$$

$$Re\{[\alpha L + \eta(1 - i\Omega\tau_p)^{\frac{1}{2}}]^{-1} e^{-i\Omega t}\}$$

The intensity of the photoluminescence to be expected can now be computed from equation (23) using the values given in Table 1. Looking for radiation at 1.5 eV, excited by radiation at 5 eV, the case of zero modulation frequency ($\Omega = 0$) reduces to:

$$\frac{dF_1}{d\omega \, d\Omega_{out}} = 9 \times 10^{-20} N_\lambda^{(1)} \quad (24)$$

With a bandwidth of $\Delta\omega = 10^{11}$ sec$^{-1}$, $$\frac{dF_1}{d\Omega_{out}} = 9 \times 10^{-9} N_\lambda^{(1)}. \quad (25)$$

For a power flux of $10^{-4}$ W/cm$^2$, when $N_\lambda^{(1)} = 1.25 \times 10^{14}$ cm$^{-2}$ sec$^{-1}$ (at $\hbar\omega_1 = 5$ eV), about a million photons per cm$^2$ and per second escape the semiconductor at the photoluminescence frequency of 1.5 eV. This flux is sufficient to permit detection by photomultipliers.

TABLE 1

The Values of Parameters Used to Evaluate the Luminescence Flux at 1.5 eV Photon Energy

| | |
|---|---|
| $\hbar\omega = 1.5$ eV | $\alpha = 1.22 \times 10^4$ cm$^{-1}$ |
| $\omega = 2.275 \times 10^{15}$ s$^{-1}$ | $\alpha_1 = 2 \times 10^6$ cm$^{-2}$ |
| n = 3.666 | $T(\eta_1) = 1 - R(\eta_1) = 0.4$ (at $\theta_{out} = 40°$) |
| $n_1 = 2.273$ | $P_0 = 5 \times 10^{-6}$ cm$^3$ (corresponding to $N_0 = 5 \times 10^{17}$ cm$^{-3}$) |
| $\hbar\omega_1 = 5$ eV | $s = 10^6$ cm s$^{-1}$ |
| $\eta = 0.985$ (corresponding to $\theta_{out} = 40°$) | L = 2 $\mu$m |
| $\eta_1 = 0.959$ (corresponding to $\theta_{out} = 40°$ | |
| $D \cong D_p = 5.2$ cm$^2$ s$^{-1}$ (corresponding to $N_0 = 5 \times 10^{17}$ cm$^{-3}$) | |

[n, n$_1$, $\alpha$ and $\alpha_1$ are derived from D. E. Aspnes et al., Phys. Rev. B 985 (1983). P$_0$ has been computed from equation A6 of O. von Roos, J. Appl. Phys. 54, 1390 (1983), using $n_i = 1.9 \times 10^6$ cm$^{-3}$; the value of L comes from H. C. Casey, Jr., et al., J. Appl. Phys. 44, 1281 (1973); the transmissivity (T($\eta_1$)) has been computed from the formula given in M. Born, et al., Principles of Optics, 5th Edition, Pergamon Press, Oxford, p. 616 (1975), using paragraph 13.2 on page 615 and assuming $n_1 = 2.273$ and $\kappa_1 = 4.084$; and T($\theta_1$) has been computed as a function of $\theta_{out} = \theta_0$ and is seen to be polarization independent for $\theta_0 < 50$ degrees.]

The determination of the phase shift and the lifetime ($\tau_p$) proceeds according to the following procedure, which is similar in some ways to that described in O. von Roos, J. Appl. Phys. 50, 3738 (1979). Taking the real part of the quantity in braces in equation (23), we have $$Re\{[\alpha L + \eta(1 - i\Omega\tau_p)^{\frac{1}{2}}]^{-1} e^{i\Omega t}\} = F_1(\Omega)\cos\Omega t + F_2(\Omega)\sin\Omega t. \quad (26)$$

where $$F_1(\Omega) = \frac{\alpha L + \eta A}{(\alpha L + \eta A)^2 + (\eta B)^2}. \quad (27a)$$

$$F_2(\Omega) = \frac{\eta B}{(\alpha L + \eta A)^2 + (\eta B)^2}. \quad (27b)$$

with $$A = \frac{1}{\sqrt{2}}(1 + \sqrt{1 + \Omega^2\tau_p^2})^{\frac{1}{2}}. \quad (27c)$$

$$B = \frac{\Omega\tau_p}{\sqrt{2}}(1 + \sqrt{1 + \Omega^2\tau_p^2})^{-\frac{1}{2}}$$

Equation (26) gives the time dependence of the luminescence signal. If we now mix this signal with a signal of the form cos ($\Omega t + \phi$) derived from the original modulation, where $\phi$ is an arbitrary but constant phase shift, we obtain the following dc component containing phase shift information:

$$F_{dc} = F_1(\Omega)\cos\phi + F_2(\Omega)\sin\phi. \quad (28)$$

Now, forming the integrals $$\frac{1}{\pi}\int_\alpha^{2\pi+\alpha}\cos\phi\, F_{dc}\, d\phi = F_1(\Omega), \text{ and} \quad (29a)$$

$$\frac{1}{\pi}\int_\alpha^{\alpha+2\pi}\sin\phi\, F_{dc}\, d\phi = F_2(\Omega), \quad (29b)$$

yields the functions $F_1$ and $F_2$. This procedure may be repeated at different modulation frequencies if $\Omega\tau_p$ turns out to be too large. For small $\Omega\rho_p$, it follows that $$F_1 = \frac{1}{\alpha L + \eta}, \text{ and } F_2 = \frac{\eta}{2}\frac{\Omega\tau_p}{(\alpha L + \eta)^2}; \quad (30)$$

and consequently $$\Omega\tau_p = \frac{2}{\eta} F_2 F_1^{-2} \quad (31)$$

If, upon substituting values for $F_1$ and $F_2$, it appears that $\Omega\tau_p$ is too large to support the above assumption, the procedure can be repeated at a different (lower) modulation frequency.

In Table 2, values of $F_1$ and $F_2$ are given for various assumed values of $\Omega\tau_p$, using parameter values from Table 1. Also shown are values of $\Omega\tau_p$ recalculated from equation (31). We see that the error is fairly small, even at $\Omega\tau_p = 1$. Thus, the procedure is fairly insensitive to the assumption that $\Omega\tau_p$ is small. Since $\tau_p$ is between approximately $10^{-8}$ and $10^{-9}$ seconds, as described in H. C. Casey, et al., J. Appl. Phys. 44, 1281 (1973), we are considering modulation frequencies of the order $2\pi\nu\tau_p \simeq 0.1$ or $\nu \frac{1}{4} 1.6-16$ MHz. Frequencies of that order are easy to manage.

TABLE 2

The functions $F_1$ and $F_2$ of equations (27) calculated with parameter values from Table 1 as a function of $\Omega\tau_p$, and a recalculation of $\Omega\tau_p$ using equation (31).

| $\Omega\tau_p$ | $F_1$ | $F_2$ | eq. (31) | error in % |
|---|---|---|---|---|
| 0.1 | 0.2918 | 0.0042 | 0.0999 | 0.01 |
| 0.3 | 0.2905 | 0.0124 | 0.2973 | 0.3 |
| 0.6 | 0.2867 | 0.0235 | 0.5804 | 2 |
| 0.8 | 0.2832 | 0.0299 | 0.7575 | 4 |
| 1.0 | 0.2794 | 0.0356 | 0.9249 | 7.5 |

The procedure discussed above is predicated on a knowledge of the magnitude of the intensity of the luminescence radiation (equation (23)). A different method, which avoids the need for this calibration, is to simply take the ratio $F_1/F_2$. From equations 30 we obtain $$F_2/F_1 = \frac{\eta}{2}\Omega\tau_p/(\alpha L + \eta). \quad (32)$$

since $$L = \sqrt{D\tau_p}. \quad (33)$$

Equation (32) constitutes a quadratic equation for the determination of $\tau_p$, once the diffusion constant D (eg (7)) has been estimated.

According to the preceeding analysis, it is possible to estimate the lifetime of minority carriers in GaAs by monitoring the photoluminescence induced by an intensity modulated light beam. The analysis leads to rather simple results, provided that certain prerequisites are met. The frequency of the exciting light must be rather high (for GaAs, $\hbar\omega_1 \simeq 5$ ev, corresponding to a wavelength of 2500 angstroms), so that absorption is high. The radiation beam spot must be at least on the order of 1 cm$^2$ and illumination must be fairly uniform. However, the power requirements are modest. An intensity of 0.1 mW/cm$^2$ for the modulated part of the light beam is sufficient. Photomultipliers at the luminescence frequency ($\simeq 1.5$ eV) and associated electronics capable of handling signals of approximately 10 MHz are available.

While certain specific embodiments of the invention have been disclosed as typical, the invention is not limited to these particular forms, but rather is applicable broadly to all such variations as fall within the scope of the appended claims. For example, the various components of the apparatus 50 may be any suitable components able to perform the functions described herein. The acquisition and design of such components are well within the capabilities of a worker skilled in the art.

Some other direct band-gap semiconductors suitable for analysis by the method of the present invention are listed in Table 3, along with values of their bandgaps at room temperature.

TABLE 3

Three direct gap semiconductors other than GaAs suitable for lifetime measurements according to the described method.

| Semiconductor | Band-Gap at Room Temperature (eV) |
|---|---|
| GaSb | 0.67 |
| InP | 1.27 |

TABLE 3-continued

Three direct gap semiconductors other than GaAs suitable for lifetime measurements according to the described method.

| Semiconductor | Band-Gap at Room Temperature (eV) |
| --- | --- |
| InAs | 0.36 |

What is claimed is:

1. A method of measuring minority carrier lifetime in a direct band-gap semiconductor having a preselected energy gap, comprising:
    producing luminescence radiation within a sample of the semiconductor by irradiating the sample with incident photon radiation having a characteristic energy at least as great as said energy gap;
    modulating the intensity of the incident radiation according to a simple sinusoidal wave form having a frequency of at least 1.6 megahertz to induce modulation of the luminescence radiation at a phase shifted from the incident radiation;
    detecting the luminescence radiation; and
    isolating information as to the amount by which the phase of the luminescence radiation is shifted relative to the incident radiation, as a measure of minority carrier lifetime.

2. The method of claim 1 wherein:
    the phase shift information is isolated by comparison to a reference signal modulated at said frequency.

3. The method of claim 2, wherein:
    the phase shift information is summed over a $2\pi$ range in the phase of the reference signal.

4. The method of claim 1, wherein:
    the step of detecting luminescence radiation comprises transforming the radiation to a modulated electrical signal; and
    the phase shift information is isolated by mixing said electrical signal with a reference electrical signal modulated at said frequency and having a phase which is known relative to the phase of the incident radiation, and isolating a direct current component of the mixed signal.

5. The method of claim 4, wherein:
    the minority carrier lifetime is calculated by varying the phase of the reference signal over a range of $2\pi$ radians and integrating the direct current component over said $2\pi$ range.

6. The method of claim 1, wherein:
    the direct band-gap semiconductor is chosen from a group consisting of GaAs, $Al_xGA_{(1-x)}As$ (with x<0.44), GaSb, InAs and InP.

7. The method of claim 1 wherein:
    the direct band-gap semiconductor is GaAs.

8. The method of claim 7 wherein:
    the incident radiation is modulated at a frequency of approximately 100 megahertz.

9. The method of claim 1 wherein the detecting step comprises:
    detecting on a selective basis radiation having a characteristic energy less than said energy gap.

10. The method of claim 9 wherein the selective detection step comprises:
    filtering the luminescence radiation to exclude radiation reflected by the sample; and
    exposing a photodetector to the filtered radiation.

11. Apparatus for measuring minority carrier lifetime in a direct band-gap semiconductor having a preselected energy gap, comprising:
    means for irradiating a sample of the semiconductor with incident photon radiation having a characteristic energy at least as great as said energy gap, such that luminescence radiation is generated within the sample;
    means for modulating the intensity of the incident radiation according to a simple sinusoidal waveform having a frequency of at least 1.6 megahertz to induce modulation of the luminescence radiation at a phase shifted from the incident radiation;
    means for detecting the luminescence radiation; and
    means for isolating information as to the amount by which the phase of the luminescence radiation is shifted relative to the incident radiation, and using that information to calculate minority carrier lifetime.

12. The apparatus of claim 11 wherein:
    the means for detecting luminescence radiation comprises means for transforming the radiation to a modulated electrical signal; and
    the means for isolating information as to the amount by which the phase is shifted comprises means for mixing said electrical signal with a reference electrical signal modulated at said frequency and having a phase which is known relative to the phase of the incident radiation.

13. The apparatus of claim 12, wherein:
    the information isolation means further comprises means for isolating a direct current component of the mixed signal.

14. The apparatus of claim 12 which further comprises:
    means for varying the phase of the reference signal and integrating said direct current component over a range of $2\pi$ radians.

* * * * *